US010013758B2

(12) United States Patent
Koceski et al.

(10) Patent No.: US 10,013,758 B2
(45) Date of Patent: Jul. 3, 2018

(54) SYSTEMS AND METHODS FOR ASSESSING NERVE INFLAMMATION BASED ON A SEGMENTED MAGNETIC RESONANCE IMAGE VOLUME

(71) Applicants: Saso Koceski, Skopje (MK); Filip Shteriev, Skopje (MK); Domenico Ciambrone, L'Aquila (IT); Lionel Lenkinski, Toronto (CA); Robert Lenkinski, Dallas, TX (US)

(72) Inventors: Saso Koceski, Skopje (MK); Filip Shteriev, Skopje (MK); Domenico Ciambrone, L'Aquila (IT); Lionel Lenkinski, Toronto (CA); Robert Lenkinski, Dallas, TX (US)

(73) Assignee: 3D Imaging Partners, Toronto, Ontario ( * ) Notice: Subject to any disclaimer, the term of this patent is extended or adjusted under 35 U.S.C. 154(b) by 224 days.

(21) Appl. No.: 15/167,098

(22) Filed: May 27, 2016

(65) Prior Publication Data
US 2016/0350917 A1 Dec. 1, 2016

Related U.S. Application Data

(60) Provisional application No. 62/167,967, filed on May 29, 2015.

(51) Int. Cl.
| | | |
|---|---|---|
| G06K 9/00 | (2006.01) | |
| G06T 7/00 | (2017.01) | |
| A61B 5/00 | (2006.01) | |
| A61B 5/055 | (2006.01) | |

(52) U.S. Cl.
CPC ............ *G06T 7/0012* (2013.01); *A61B 5/055* (2013.01); *A61B 5/4041* (2013.01); *A61B 5/7282* (2013.01); *G06T 2207/10088* (2013.01); *G06T 2207/30004* (2013.01)

(58) Field of Classification Search
None
See application file for complete search history.

(56) References Cited

U.S. PATENT DOCUMENTS

| | | | | | |
|---|---|---|---|---|---|
| 6,031,935 | A | * | 2/2000 | Kimmel | G06K 9/48 382/170 |
| 6,120,461 | A | * | 9/2000 | Smyth | A61B 3/113 348/E13.041 |
| 2011/0288400 | A1 | * | 11/2011 | Russell | A61B 5/055 600/411 |
| 2012/0177262 | A1 | * | 7/2012 | Bhuiyan | A61B 3/0025 382/128 |

(Continued)

*Primary Examiner* — Shervin Nakhjavan
(74) *Attorney, Agent, or Firm* — Quarles & Brady LLP

(57) ABSTRACT

Systems and methods for processing a segmented volume from magnetic resonance images that corresponds to a nerve are provided. The segmented volume can be processed to generate a report that provides complementary information on the state or condition of tissues contained in the segmented nerve volume. For example, the segmented volume can be processed to identify regions of suspected inflammation, or other pathology such as demyelination, of the nerve tissue contained in the segmented volume. The systems and methods described here provide a user-defined approach to identifying regions of suspected inflammation, or other pathology, in a segmented nerve volume.

10 Claims, 5 Drawing Sheets

(56) References Cited

U.S. PATENT DOCUMENTS

| | | | | |
|---|---|---|---|---|
| 2013/0121548 A1* | 5/2013 | Kovalan | ................. | G06T 15/08 |
| | | | | 382/128 |
| 2014/0119624 A1* | 5/2014 | Ehlers | ................. | A61B 5/0066 |
| | | | | 382/131 |
| 2015/0029464 A1* | 1/2015 | Jayasundera | ......... | G06T 7/0016 |
| | | | | 351/246 |

* cited by examiner

SYSTEMS AND METHODS FOR ASSESSING NERVE INFLAMMATION BASED ON A SEGMENTED MAGNETIC RESONANCE IMAGE VOLUME

CROSS-REFERENCE TO RELATED APPLICATIONS

This application claims the benefit of U.S. Provisional Patent Application Ser. No. 62/167,967, filed on May 29, 2015, and entitled "SYSTEMS AND METHODS FOR ASSESSING NERVE INFLAMMATION BASED ON A SEGMENTED MAGNETIC RESONANCE IMAGE VOLUME."

BACKGROUND OF THE INVENTION

The field of the invention is systems and methods for the segmentation of anatomy in medical images, and for the analysis of those segmentations. More particularly, the invention relates to systems and methods for nerve segmentation in images acquired with magnetic resonance imaging ("MRI").

Nerve segmentation is an attractive clinical goal because allowing clinicians to accurately and non-invasively visualize the three-dimensional structure of a nerve can improve surgical planning and guidance, as well as improve treatment and diagnosis of pathologies associated with a nerve.

Recently, a nerve segmentation technique was described in co-pending U.S. Patent Application No. 2014/0328529. This technique allows rapid and accurate segmentation of a nerve volume from a magnetic resonance image volume, or series of contiguous magnetic resonance images. There remains a need, however, to provide clinical utility to the visualization of a segmented nerve volume. For instance, it is desirable to provide a visualization of regions in a segmented nerve volume that may be associated with suspected inflammation or other pathology, such as demyelination.

SUMMARY OF THE INVENTION

The present invention overcomes the aforementioned drawbacks by providing systems and method for analyzing a segmented nerve volume to identify regions in the nerve volume that indicate suspected inflammation or other pathology.

It is thus an aspect of the invention to provide a computer-implemented method for generating a report that indicates regions of suspected pathology in a nerve. A segmented nerve volume is provided to a computer system, and a first histogram is generated based on a cross-section through the segmented nerve volume. A threshold value is selected based on the first histogram, and a second histogram is generated based on image intensity values in the segmented nerve volume that satisfy a condition based on the selected threshold value. A report that indicates regions of suspected pathology in the segmented nerve volume is then generated. The report is generated based in part on the second histogram and the segmented nerve volume.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Described here are systems and methods for processing a segmented volume from magnetic resonance images that corresponds to a nerve. The segmented volume can be processed to generate a report that provides complementary information on the state or condition of tissues contained in the segmented nerve volume. For example, the segmented volume can be processed to assess a degree of inflammation in the nerve tissue contained in the segmented volume. The systems and methods described here provide a user-defined approach to identifying regions of suspected inflammation, or other pathology, in a segmented nerve volume.

Figure 1:
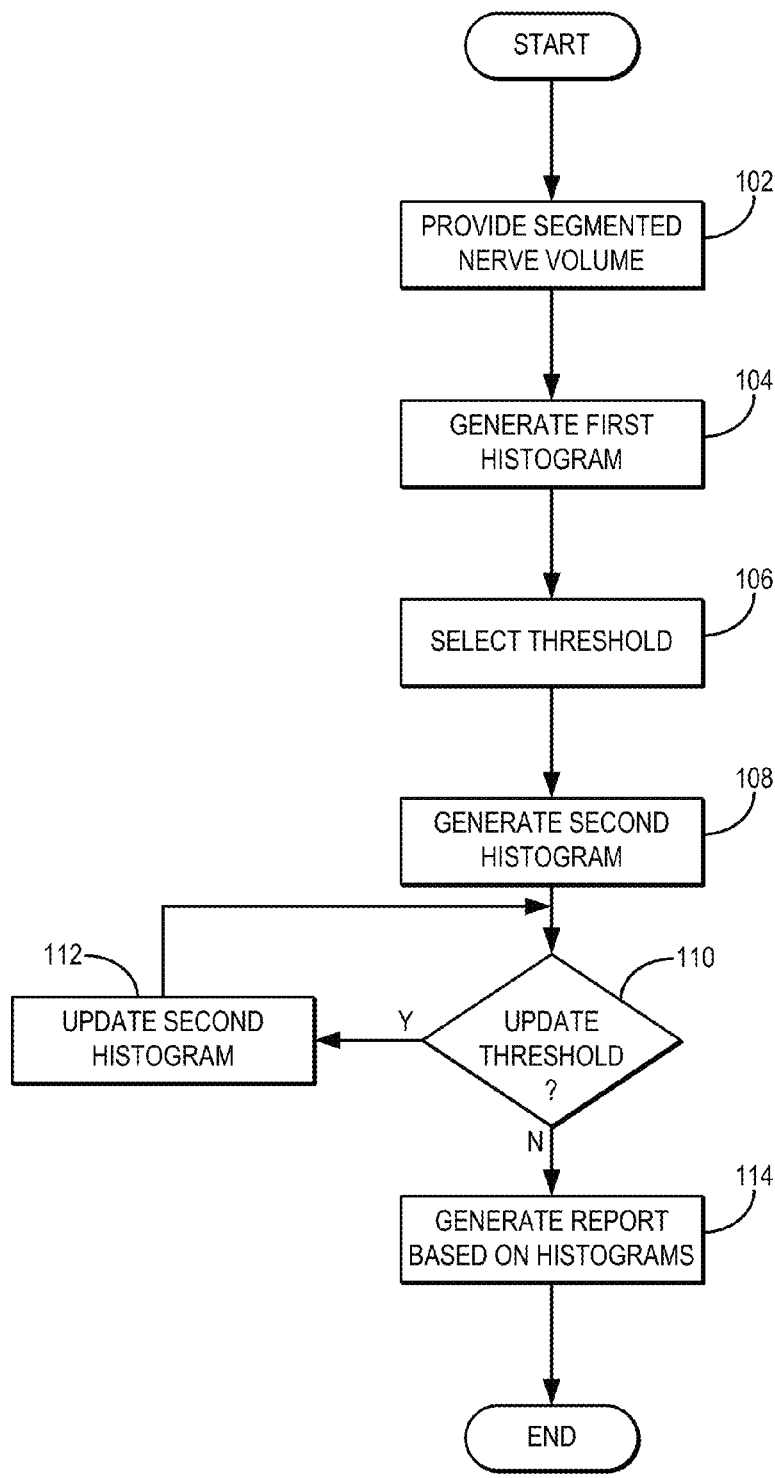
FIG. 1 is a flowchart setting forth the steps of an example method for generating a report that indicates regions of suspected inflammation, or other pathology, in a segmented nerve volume.

Referring now to FIG. 1, a flowchart is illustrated as setting forth the steps of an example method for analyzing a segmented nerve volume to identify regions of suspected inflammation, or other pathology, within the nerve volume. The method begins by providing a segmented nerve volume, as indicated at step 102. In general, the segmented nerve volume is a volume-of-interest that has been segmented from a three-dimensional magnetic resonance image volume, or from a series of contiguous, two-dimensional magnetic resonance images. The segmented nerve volume therefore contains magnetic resonance image intensity values that are associated with a nerve segmented from a larger magnetic resonance image volume.

In one example, the segmented nerve volume can be provided by retrieving a previously generated nerve volume from storage. In another example, the segmented nerve volume can be provided by generating the nerve volume from magnetic resonance images or magnetic resonance image volumes that have been acquired with an MRI system.

Preferably, the images associated with the segmented nerve volume are acquired using both a T1-weighted pulse sequence and a T2-weighted pulse sequence. Moreover, these T1-weighted and T2-weighted images are preferably co-registered. As such, the segmented nerve volume can selectively contain either T1-weighted image intensity values or T2-weighted image intensity values, depending on whether the segmented nerve volume is applied to the T1-weighted images or T2-weighted images.

Using the segmented nerve volume, a first histogram is generated, as indicated at step 104. Preferably, the first histogram is generated based on T2-weighted images; however, images with other image contrasts (e.g., T1-weighting, diffusion weighting) can also be used in some configurations. This first histogram is constructed to bin image intensity values for a single section of the nerve volume that is perpendicular to the segmented nerve axis. Based on user input, the selected nerve section for which the first histogram was generated can be changed and the first histogram correspondingly updated.

In general, the first histogram contains a number of bins corresponding to the range of signal intensities in the cross-sectional image from which the first histogram is generated. For instance, the signal intensity values can range from 0 to 4095 for a DICOM image.

As one example, the first histogram is generated based on pixels contained only within the nerve contour in the segmented nerve volume. That is, the cross section through the segmented nerve volume represents a cross-sectional image that can be divided into two parts: an interior region containing pixels inside the nerve contour, and an exterior region containing pixels outside the nerve contour. In some embodiments, an image mask can be applied to this cross-sectional image to mask those pixels in the exterior region, leaving only the pixels in the interior region to be used for generating the first histogram.

In this example, if $NI_i$ is the total number of pixels in the masked interior region on the cross-sectional slice and k is the total number of bins, the first histogram, $m_{ij}$, meets the following conditions:

$$NI_i = \sum_{j=1}^{k} m_{ij}. \quad (1)$$

A threshold value to be applied to the first histogram is then selected, as indicated at step 106. The selected threshold defines values in the first histogram that are over the threshold and values in the first histogram that are under the threshold.

In one example, this threshold value can be selected based on a user input, such as by a user inputting a value for the threshold or by selecting the threshold value using a slider bar or other graphical user interface object to set the threshold value.

In another example, the threshold can be automatically selected. The first histogram should generally follow a Gaussian (i.e., normal) distribution. A normal distribution curve can be fit to the first histogram to estimate a local threshold value for a given cross-sectional image. For example, a maximum-likelihood estimation can be used to estimate the best fit of the normal distribution to the first histogram. Based on this fit, the local threshold, $T_i$, for the first histogram corresponding to a particular cross-sectional image can be defined as follows:

$$T_i = \mu + \sigma_i \quad (2);$$

where $\mu$ is a mean value and $\sigma_i$ is the estimated standard deviation for the $i^{th}$ cross-sectional image. Using local threshold values for a number, n, of cross-sectional images (e.g., the number of cross-sectional images along the length of the nerve) a global threshold, T, can be estimated as follows:

$$T = \max [T_1, T_2, \ldots, T_i, \ldots, T_n] \quad (3).$$

The automatically selected global threshold defines values in the first histogram that are over the threshold and values in the first histogram that are under the threshold. The information from this threshold, whether manually or automatically selected, will be used to generate a second histogram that can be used to indicate suspected inflammation, or other pathology, in the segmented nerve volume.

Thus, a second histogram that is based at least in part on the selected threshold value is generated, as indicated at step 108. In general, the second histogram is constructed to bin the number of image intensity values in a cross-section through the segmented nerve volume that are above the selected threshold value.

As one example, each bin in the second histogram corresponds to a perpendicular section through the nerve volume, and the value for each bin is computed as the normalized value of the number of image intensity values in that cross-section that are above the threshold value that was selected based on the first histogram. Accordingly, changing the selected threshold will update the second histogram; thus, as indicated at decision block 110, the user can update the selected threshold value and the second histogram will be correspondingly updated, as indicated at step 112.

Once the second histogram is generated, a Poisson regression model can be applied to the bins in the second histogram. The Poisson regression assumes that the responsible variable, Y, has a Poisson distribution, and assumes the logarithm of its expected value can be modeled by a linear combination of unknown parameters.

If $x \in R^n$ is a vector of independent variables, then the model can take the form, $$\log(E(Y|x)) = \alpha + \beta' x \quad (4);$$

where $\alpha \in R$ and $\beta \in R^n$. The expression in Eqn. (4) can be rewritten as, $$\log(E(Y|x)) = \theta' x \quad (5);$$

where x is now an (n+1) dimensional vector of n independent variables concatenated to a vector of ones. In Eqn. (5), the parameter $\theta$ is $\alpha$ concatenated to $\beta$. Thus, when given a Poisson regression model, $\theta$, and an input vector, x, the predicted mean of the associated Poisson distribution is given by, $$E(Y|x) = e^{74 \, ' x} \quad (6).$$

If $Y_i$ are independent observations with corresponding values $x_i$ of the predictor variables, then $\theta$ can be estimated by a maximum likelihood estimation technique. Once $\theta$ is estimated, the median value, $\lambda$, and its bounds, $\nu$, can be defined as, $$\lambda - \ln 2 \leq \nu < \lambda + \frac{1}{3} \quad (7).$$

All of the bins falling into the median bounds are potentially treated as regions of suspected inflammation.

For a given second histogram, a report can be generated, as indicated at step 114. In general, the report can indicate regions of suspected inflammation, or other pathology, in the segmented nerve volume. As one example, the generated report can include a display on a graphical user interface that allows selective visualization of the regions of suspect inflammation, or other pathology. For instance, pixels associated with one of the regions can be color-coded and overlaid on a magnetic resonance image or in the segmented nerve volume.

A clinician can then view report and use the information conveyed in the report to complement his or her professional opinion on the possible diagnosis of inflammation, or other pathology, in the nerve. Accordingly, the report generated using the aforementioned method can be useful for diagnostic support, treatment planning, surgical guidance, or combinations thereof.

Figure 2A:
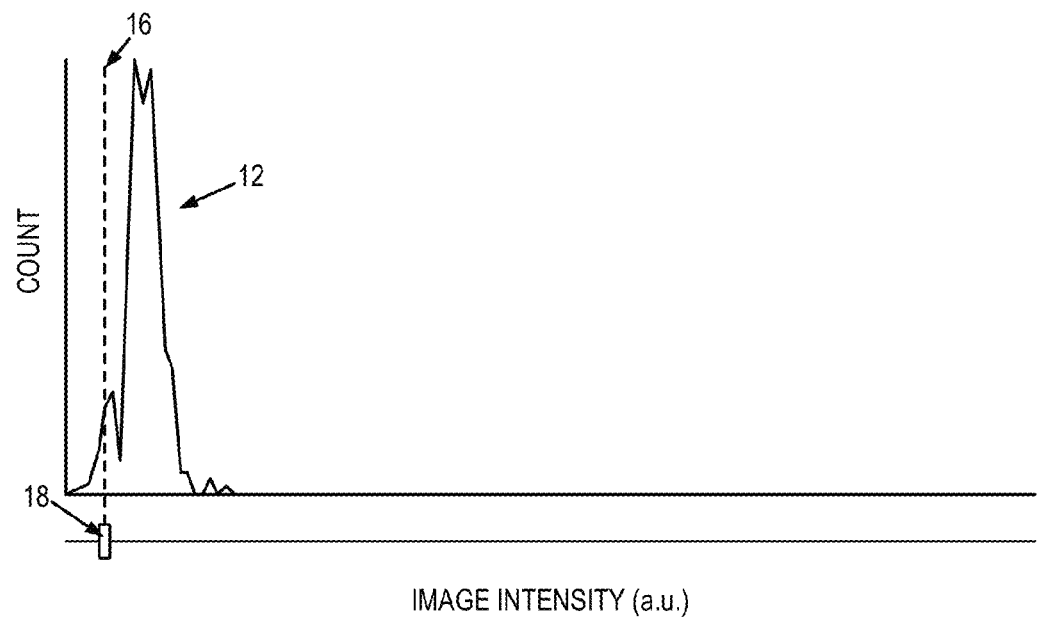
FIG. 2A is an example of a first histogram generated for a cross-section through a segmented nerve volume and whose bins are based on image intensity values in the cross-section.
Figure 2B:
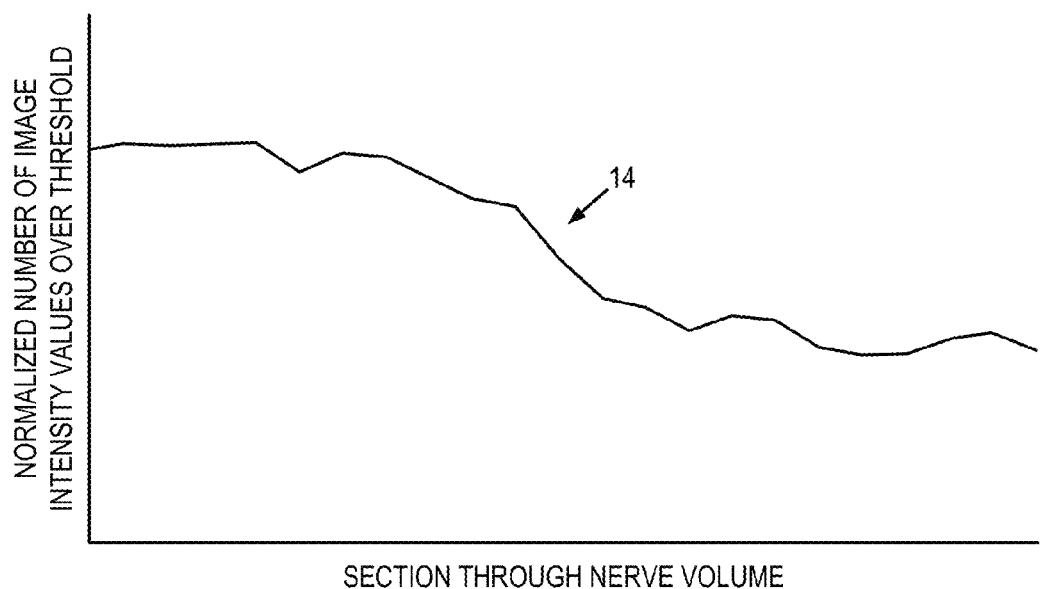
FIG. 2B is an example of a second histogram generated for the segmented nerve volume and whose bins are based on image intensity values in the segmented nerve volume that are at or above a selected threshold.

Referring now to FIGS. 2A and 2B, an example of a first histogram 12 and a second histogram 14 are illustrated. As described above, the first histogram 12 is based on a single section through the segmented nerve volume, whereas the second histogram 14 is based on the entire segmented nerve volume, or a subvolume thereof. In this example, the selected threshold 16 can be selected based on user adjustment of a slider bar 18 that is displayed to a user on a graphical user interface 20. Adjustment of the slider bar 18 correspondingly changes the value of the selected threshold 16.

Figure 3A:
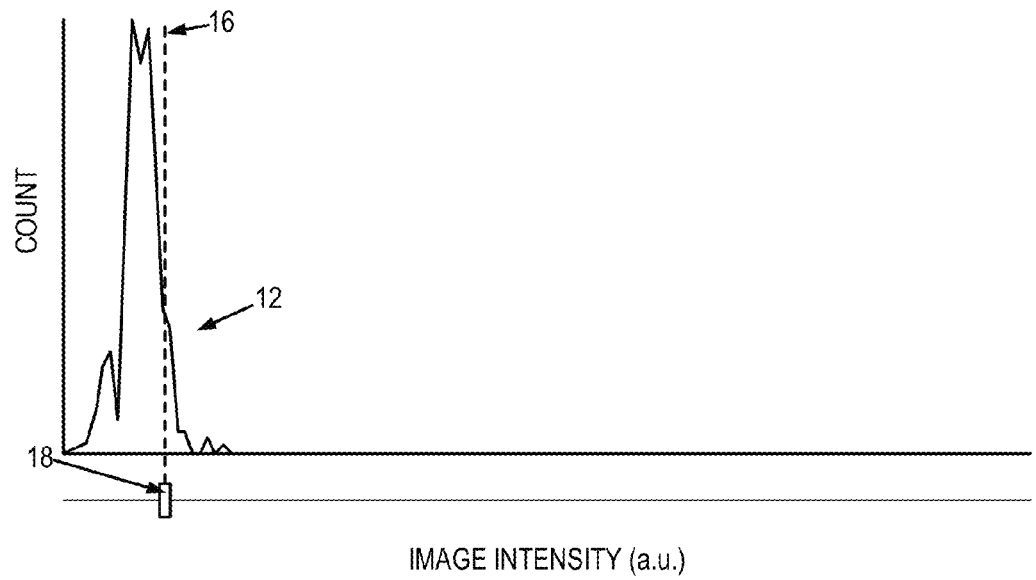
FIG. 3A is an example of the first histogram of FIG. 2A indicating an updated threshold value.
Figure 3B:
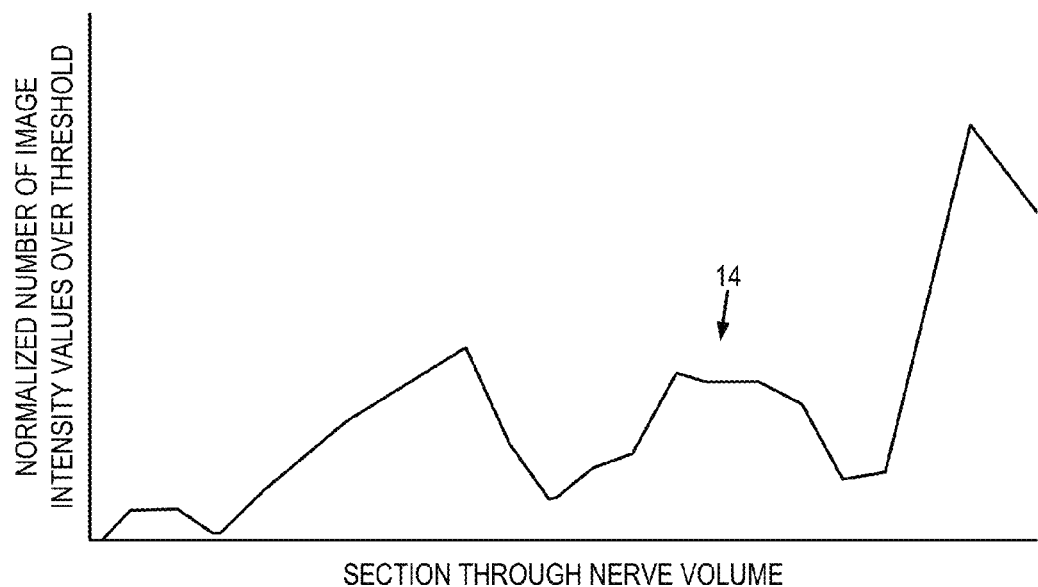
FIG. 3B is an example of an updated second histogram that is generated based on the updated threshold value indicated in FIG. 3A.

Referring now to FIGS. 3A and 3B, an example of a first histogram 12 and a second histogram 14 are illustrated. In this example, the slider bar 18 has been adjusted to change the threshold 16. Because the second histogram 14 is generated based, at least in part, on the threshold 16, the second histogram 14 illustrated in FIG. 3B has been updated relative to the second histogram 14 illustrated in FIG. 2B.

Figure 4:
FIG. 4 is an example of a graphical user interface displaying a cross-section image, a first histogram generated from the cross-section image, a three-dimensional image volume on which a segmented nerve volume is overlaid, a second histogram, and three orthogonal views through the three-dimensional image volume.

Referring now to FIG. 4, an example graphical user interface ("GUI") that can be used in connection with the method described above is illustrated. The GUI can include a display of a cross-sectional image 50 that is perpendicular to a nerve axis running through a segmented nerve volume 52. In the cross-sectional image 50, a nerve 54 is displayed along with surrounding anatomical structures 56.

The GUI can also include a display of a three-dimensional image volume 58 that depicts the nerve 54 and the surrounding anatomical structures 56. As illustrated in FIG. 4, the display of the three-dimensional image volume 58 can be supplemented by overlaying the segmented nerve volume 52 on the magnetic resonance image volume.

The GUI can also include a display of orthogonal images in the three-dimensional magnetic resonance image volume. For example, a transverse image 60, a coronal image 62, and a sagittal image 64 can all be displayed. Each of these displays can be augmented to indicate the relative locations of the other displays. For example, the transverse image display 60 can be augmented to display orthogonal lines 66 and 68, where line 66 indicates the plane through which the coronal image display 62 is viewed and line 68 indicates the plane through which the sagittal image display 68 is viewed. These displays 60, 62, 64 can be individually adjusted to visualize different cross-sections through the three-dimensional image volume.

When a user selects a cross-sectional image 50 to be processed, a first histogram 12 is generated and displayed. Optionally, a slider bar 18 is provided to allow user-selection and adjustment of a threshold value, as described above. On selection of the threshold value, a second histogram 14 is generated and displayed. The visualization of the nerve 54 can then be augmented to indicate regions of suspected inflammation, or other pathology, based on the second histogram. For example, the visualization of the nerve 54 in the cross-sectional image display 50, transverse image display 60, coronal image display 62, and sagittal image display 64 can be augmented to color-code pixels in these displays that have image intensity values indicated by the second histogram as representing suspected inflammation, or other pathology. In some embodiments, each of these augmented visualizations of the nerve can constitute a report that is generated based on the second histogram.

Figure 5:
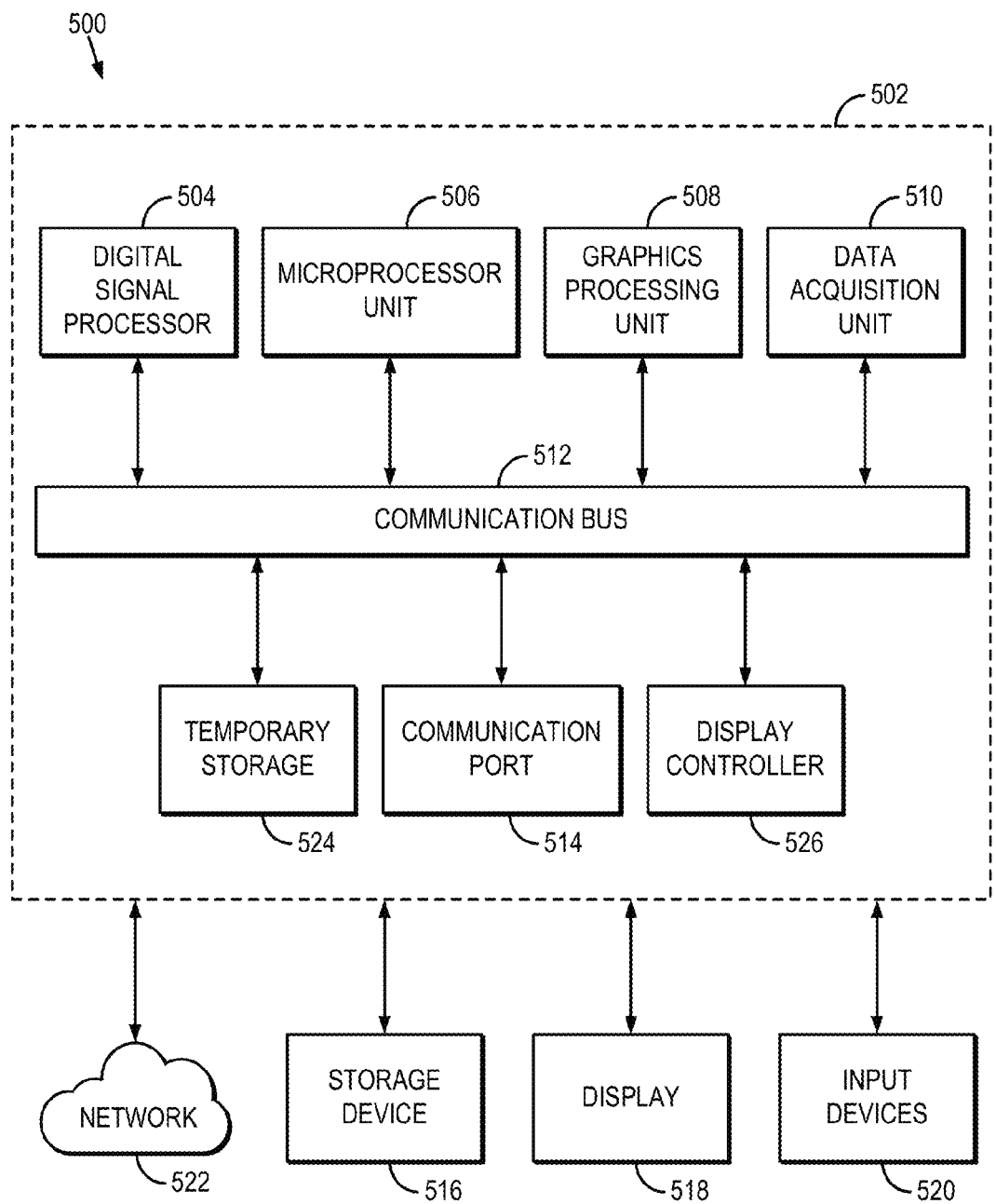
FIG. 5 is a block diagram of an example computer system that includes an image processing unit that can be configured to implement the methods described herein.

Referring now to FIG. 5, a block diagram of an example computer system 500 that can be configured to analyze a segmented nerve volume to identify regions of suspected inflammation, or other pathology, within the nerve volume, as described above, is illustrated. The segmented nerve volume and any associated magnetic resonance images can be provided to the computer system 500 from a magnetic resonance imaging ("MRI") system, or from a data storage device, and are received in a processing unit 502.

In some embodiments, the processing unit 502 can include one or more processors. As an example, the processing unit 502 may include one or more of a digital signal processor ("DSP") 504, a microprocessor unit ("MPU") 506, and a graphics processing unit ("GPU") 508. The processing unit 502 can also include a data acquisition unit 510 that is configured to electronically receive data to be processed, which may include segmented nerve volumes and magnetic resonance images, image series, or image volumes. The DSP 504, MPU 506, GPU 508, and data acquisition unit 510 are all coupled to a communication bus 512. As an example, the communication bus 512 can be a group of wires, or a hardwire used for switching data between the peripherals or between any component in the processing unit 502.

The DSP 504 can be configured to receive and processes the segmented nerve volume and any associated magnetic resonance images. The MPU 506 and GPU 508 can also be configured to process the segmented nerve volume and any associated magnetic resonance images in conjunction with the DSP 504. As an example, the MPU 506 can be configured to control the operation of components in the processing unit 502 and can include instructions to perform processing of segmented nerve volume and any associated magnetic resonance images on the DSP 504. Also as an example, the GPU 508 can process image graphics.

In some embodiments, the DSP 504 can be configured to process the segmented nerve volume and any associated magnetic resonance images received by the processing unit 502 in accordance with the methods and algorithms described above. Thus, the DSP 504 can be configured to generate first and second histograms and to generate a report that indicates regions of suspected inflammation, or other pathology, in the segmented nerve volume.

The processing unit 502 preferably includes a communication port 514 in electronic communication with other devices, which may include a storage device 516, a display 518, and one or more input devices 520. Examples of an input device 520 include, but are not limited to, a keyboard, a mouse, and a touch screen through which a user can provide an input. In one example implementation, the input device 520 can include a slider bar on a graphical user interface that allows user-selection and adjustment of a threshold value associated with the first histogram and used to generate the second histogram.

The storage device 516 is configured to store images and segmented nerve volumes, whether provided to or processed by the processing unit 502. The display 518 is used to display images, such as images that may be stored in the storage device 516, and other information. For example, the display 518 can be used to display the graphical user interface and associated images and information that are illustrated in FIG. 4. Thus, in some embodiments, the storage device 516 and the display 518 can be used for displaying the a segmented nerve volume and any associated magnetic resonance image; the first and second histograms; and the generated report indicating regions of suspected inflammation, or other pathology, in the segmented nerve volume.

The processing unit 502 can also be in electronic communication with a network 522 to transmit and receive data, magnetic resonance images, segmented nerve volumes, and other information. The communication port 514 can also be coupled to the processing unit 502 through a switched central resource, for example the communication bus 512.

The processing unit 502 can also include a temporary storage 524 and a display controller 526. As an example, the temporary storage 524 can store temporary information. For instance, the temporary storage 524 can be a random access memory.

The present invention has been described in terms of one or more preferred embodiments, and it should be appreciated that many equivalents, alternatives, variations, and modifications, aside from those expressly stated, are possible and within the scope of the invention.

The invention claimed is:

1. A computer-implemented method for generating a report that indicates regions of suspected pathology in a nerve, the steps of the method comprising:
    (a) providing a segmented nerve volume to a computer system;
    (b) generating with the computer system, a first histogram based on a cross-section through the segmented nerve volume;
    (c) selecting a threshold value based on the first histogram;
    (d) generating with the computer system, a second histogram based on image intensity values in the segmented nerve volume that satisfy a condition based on the selected threshold value; and
    (e) generating with the computer system, a report that indicates regions of suspected pathology in the segmented nerve volume, wherein the report is generated based in part on the second histogram and the segmented nerve volume.

2. The method as recited in claim 1, wherein the first histogram generated in step (b) includes bins that contain a count of image intensity values that fall within a range of image intensity values.

3. The method as recited in claim 1, wherein step (c) includes providing user input to the computer system to select the threshold value.

4. The method as recited in claim 1, wherein step (c) includes calculating the threshold value using the first histogram.

5. The method as recited in claim 1, wherein the second histogram generated in step (d) includes bins that contain a count of image intensity values in a given cross-section through the segmented nerve volume that satisfy the condition based on the selected threshold value.

6. The method as recited in claim 5, wherein the condition based on the selected threshold value is satisfied for image intensity values above the selected threshold value.

7. The method as recited in claim 1, wherein the report generated in step (e) includes an image that depicts the nerve and wherein visualization of the regions of suspected pathology in the image are augmented to identify the regions.

8. The method as recited in claim 7, wherein the visualization of the regions of suspected pathology in the image includes color coding voxels in the image that are associated with the regions of suspected pathology.

9. The method as recited in claim 1, wherein the suspected pathology is suspected inflammation of the nerve.

10. The method as recited in claim 1, wherein the suspected pathology is suspected demyelination of the nerve.

* * * * *